(12) United States Patent  
Sasaki et al.

(10) Patent No.: US 10,024,262 B2  
(45) Date of Patent: Jul. 17, 2018

(54) AIR-FUEL RATIO CONTROL DEVICE AND AIR-FUEL RATIO CONTROL METHOD

(71) Applicant: Nissan Motor Co., Ltd., Yokohama-shi, Kanagawa (JP)

(72) Inventors: Ryousuke Sasaki, Kanagawa (JP); Tamikazu Kimura, Kanagawa (JP); Nobuyuki Suzuki, Kanagawa (JP)

(73) Assignee: Nissan Motor Co., Ltd., Yokohama-shi, Kanagawa (JP)

( * ) Notice: Subject to any disclaimer, the term of this patent is extended or adjusted under 35 U.S.C. 154(b) by 0 days.

(21) Appl. No.: 15/564,258

(22) PCT Filed: Apr. 7, 2015

(86) PCT No.: PCT/JP2015/060863  
§ 371 (c)(1),  
(2) Date: Oct. 4, 2017

(87) PCT Pub. No.: WO2016/162983  
PCT Pub. Date: Oct. 13, 2016

(65) Prior Publication Data  
US 2018/0135547 A1    May 17, 2018

(51) Int. Cl.  
*F02D 41/14* (2006.01)  
*F02N 13/00* (2006.01)  
(Continued)

(52) U.S. Cl.  
CPC ....... *F02D 41/1454* (2013.01); *F01N 13/008* (2013.01); *F02D 41/1495* (2013.01);  
(Continued)

(58) Field of Classification Search  
CPC ............. F02D 13/06; F02D 2041/1418; F02D 41/1495; F02D 41/1488; F02D 41/008;  
(Continued)

(56) References Cited

U.S. PATENT DOCUMENTS

| 4,430,191 A | 2/1984 | Sone et al. |
| 2004/0107034 A1* | 6/2004 | Togai ..................... B60K 26/04 |
| | | 701/54 |

(Continued)

FOREIGN PATENT DOCUMENTS

| JP | S63140841 A | 6/1988 |
| JP | 2003013779 | 1/2003 |
| JP | 2003254135 A | 9/2003 |
| JP | 2008014178 A | 1/2008 |

*Primary Examiner* — Lindsay Low  
*Assistant Examiner* — George Jin  
(74) *Attorney, Agent, or Firm* — Young Basile Hanlon & MacFarlane, P.C.

(57) ABSTRACT

An air-fuel ratio control device includes an air-fuel ratio sensor configured such that an output current value thereof varies linearly in accordance with an oxygen concentration, and air-fuel ratio feedback control means capable of executing air-fuel ratio feedback control for feedback-controlling a fuel injection amount on the basis of a detection value from the air-fuel ratio sensor so that exhaust gas of an internal combustion engine reaches a predetermined air-fuel ratio. The air-fuel ratio control device further includes prohibiting means for prohibiting the feedback control when the air-fuel ratio reaches or exceeds a predetermined rich air-fuel ratio. The air-fuel ratio control device permits the feedback control for a predetermined period after the air-fuel ratio reaches or exceeds the predetermined rich air-fuel ratio.

9 Claims, 6 Drawing Sheets

(51) Int. Cl.
*G01N 27/407* (2006.01)
*G01N 27/409* (2006.01)
*F01N 13/00* (2010.01)

(52) U.S. Cl.
CPC ....... *G01N 27/409* (2013.01); *G01N 27/4073* (2013.01); *F02D 41/1456* (2013.01)

(58) Field of Classification Search
CPC ............. F02D 41/0085; F02D 41/1458; F02D 41/2454; F02D 41/1454; F02D 41/1401; F02D 41/1438; F02D 41/1456; F01N 11/007; F02N 13/008; G01N 27/4073; G01N 27/409; G01N 27/41; G01N 27/4111

See application file for complete search history.

(56) References Cited

U.S. PATENT DOCUMENTS

| | | | |
|---|---|---|---|
| 2004/0127326 A1* | 7/2004 | Tajima | B60K 6/485 477/3 |
| 2007/0240695 A1 | 10/2007 | Mitsuda et al. | |
| 2007/0254772 A1* | 11/2007 | Satou | F02D 41/123 477/107 |
| 2010/0274460 A1* | 10/2010 | Kuwahara | F02D 11/105 701/99 |
| 2011/0192146 A1 | 8/2011 | Sugimoto et al. | |
| 2014/0288758 A1* | 9/2014 | Suzuki | B60L 15/2009 701/22 |

* cited by examiner

AIR-FUEL RATIO CONTROL DEVICE AND AIR-FUEL RATIO CONTROL METHOD

TECHNICAL FIELD

The present invention relates to air-fuel ratio control in an internal combustion engine.

BACKGROUND

Air-fuel ratio feedback control using a so-called air-fuel ratio sensor, the air-fuel ratio sensor being configured such that an output current value output thereby when a predetermined voltage is applied thereto varies linearly relative to an air-fuel ratio of exhaust gas, is known as air-fuel ratio control performed in an internal combustion engine. When the air-fuel ratio of the exhaust gas is richer than the stoichiometric air-fuel ratio, oxygen in an atmosphere duct of the air-fuel ratio sensor is ionized by an atmosphere side electrode, and when resulting oxygen ions move to an exhaust side electrode through a solid electrolyte layer, a current flows through the air-fuel ratio sensor. Hence, when the air-fuel ratio of the exhaust gas continues to be richer than the stoichiometric air-fuel ratio, leading to a deficiency in the amount of oxygen in the atmosphere duct, a detection value obtained by the air-fuel ratio sensor deviates to a lean side of the actual air-fuel ratio. To prevent this deviation, JP2008-14178A describes temporarily terminating the air-fuel ratio feedback control and switching to open loop control when the detection precision of the air-fuel ratio sensor deteriorates in the manner described above.

However, when the air-fuel ratio feedback control is terminated in the manner described in the above document, it is no longer possible to absorb variation in a fuel injection amount caused by individual differences in components such as a fuel injection valve. Therefore, the control precision is poorer during the open loop control than during the air-fuel ratio feedback control, and as a result, various performance indices, such as engine output, fuel efficient, and exhaust emissions, deteriorate.

SUMMARY

An object of the present invention is therefore to provide an air-fuel ratio control device and an air-fuel ratio control method with which air-fuel ratio feedback control can be executed over a wider range.

According to one embodiment of this invention, an air-fuel ratio control device including an air-fuel ratio sensor configured such that an output current value thereof varies linearly in accordance with an oxygen concentration and air-fuel ratio feedback control means configured to implement feedback control on an air-fuel ratio on the basis of a detection value from the air-fuel ratio sensor. An air-fuel ratio control device further comprising prohibiting means configured to prohibit the feedback control when the air-fuel ratio equals or exceeds a predetermined rich air-fuel ratio. However, the feedback control is permitted for a predetermined period after the air-fuel ratio reaches or exceeds the predetermined rich air-fuel ratio.

DETAILED DESCRIPTION OF THE EMBODIMENTS

An embodiment of the present invention will be described below with reference to the attached figures.

Figure 1:
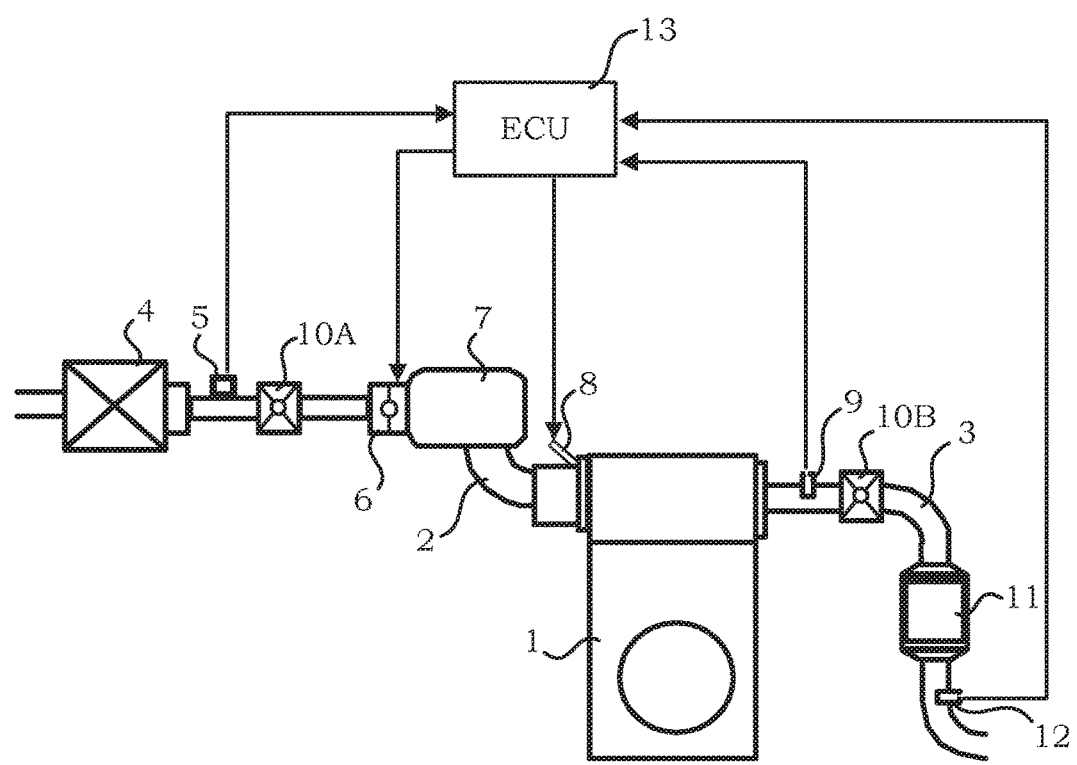
FIG. 1 is a view showing a configuration of an internal combustion engine system to which an embodiment of the present invention is applied.

FIG. 1 is a view showing a configuration of an internal combustion engine system to which an embodiment of the present invention is applied.

An air cleaner 4, an air flow meter 5, a compressor 10A of a turbocharger, a throttle chamber 6, a collector tank 7, and a fuel injection valve 8 are disposed in an intake passage 2 of an internal combustion engine 1 in order from an upstream side of an intake air flow. It should be noted that the internal combustion engine 1 according to this embodiment is a so-called port injection type internal combustion engine, but a so-called in-cylinder direct injection type internal combustion engine may be used instead.

An air-fuel ratio sensor 9, a turbine 10B of the turbocharger, a manifold catalyst 11, and an $O_2$ sensor 12 are disposed in an exhaust passage of the internal combustion engine 1 in order from an upstream side of an exhaust gas flow.

The compressor 10A and the turbine 10B are in actuality coupled to each other via a shaft so as to rotate integrally. Further, although not shown in FIG. 1, an intercooler may be disposed on a downstream side of the compressor 10A to cool air that has been pressurized by the compressor 10A so as to increase in temperature.

The air-fuel ratio sensor 9 is configured such that an output current output thereby when a voltage is applied thereto varies linearly in accordance with an oxygen concentration of the exhaust gas. The structure and characteristics of the air-fuel ratio sensor 9 will be described below.

The manifold catalyst 11 is a three-way catalyst. The $O_2$ sensor 12 generates electromotive force corresponding to the oxygen concentration of the exhaust gas. The electromotive force generated by the $O_2$ sensor 12 is approximately 0 V when the exhaust gas is leaner than the stoichiometric air-fuel ratio (also referred to simply as "when the exhaust gas is lean" hereafter), and approximately 1 V when the exhaust gas is richer than the stoichiometric air-fuel ratio (also referred to simply as "when the exhaust gas is rich" hereafter). Thus, the $O_2$ sensor 12 is configured such that an output voltage thereof varies greatly in the vicinity of the stoichiometric air-fuel ratio. In other words, the $O_2$ sensor 12 is capable of determining whether the exhaust gas is lean or rich.

Respective detection signals from the air flow meter 5, the air-fuel ratio sensor 9, and the $O_2$ sensor 12 are read by an engine controller (referred to as an ECU hereafter) 13. On the basis of these detection signals, as well as detection signals from an accelerator position sensor, a crank angle sensor, and so on, not shown in the figures, the ECU 13 controls a fuel injection amount and an ignition timing, sets a target air-fuel ratio, and executes air-fuel ratio feedback control and so on for aligning the air-fuel ratio with the target air-fuel ratio.

It should be noted that the $O_2$ sensor 12 is not used to control the internal combustion engine 1 in a state where the air-fuel ratio sensor 9 functions normally. When an abnormality occurs in the air-fuel ratio sensor 9, however, air-fuel ratio feedback control is implemented on the basis of the detection signal from the $O_2$ sensor 12.

Further, the ECU 13 implements the air-fuel ratio feedback control on each cylinder of the internal combustion engine 1. Therefore, to differentiate between the cylinders accurately, the air-fuel ratio sensor 9 is disposed in a site on the upstream side of the turbine 10B, or more specifically a site on the upstream side of the turbine 10B near a convergence portion where exhaust flow passages from the respective cylinders converge. When the air-fuel ratio sensor 9 is disposed on the downstream side of the turbine 10B, the air-fuel ratio sensor 9 detects the air-fuel ratio of the exhaust gas after the exhaust gas has converged and passed through the turbine 10B such that mixing of the exhaust gas has progressed, and as a result, it is difficult to differentiate between the cylinders.

Next, the air-fuel ratio sensor 9 will be described.

Figure 2:
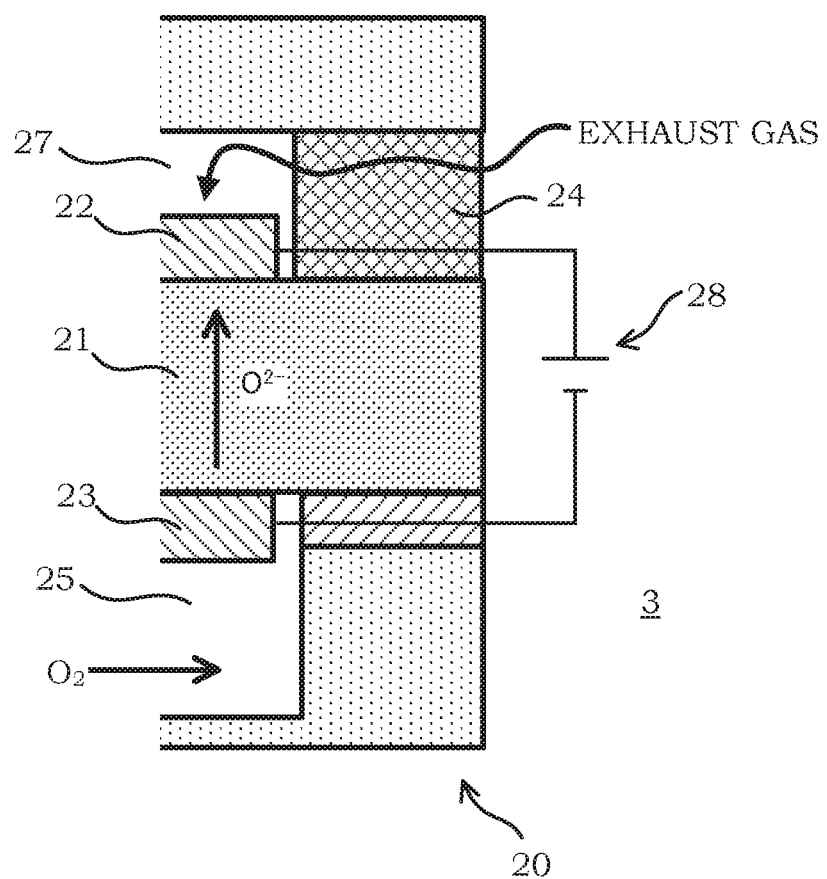
FIG. 2 is a sectional view of an air-fuel ratio sensor.

FIG. 2 is a sectional view showing a sensor element 20 of the air-fuel ratio sensor 9. It should be noted that a cover covering the sensor element 20 and a heater for heating the sensor element 20 have been omitted from FIG. 2.

The sensor element 20 is configured to include a solid electrolyte layer 21, an exhaust side electrode 22 provided on an exhaust side of the solid electrolyte layer 21, an atmosphere side electrode 23 provided on an atmosphere side of the solid electrolyte layer 21, and a diffusion resistance layer 24.

The solid electrolyte layer 21 is formed from a substance through which oxygen ions can move, for example zirconia or the like.

The exhaust side electrode 22 is disposed within an exhaust gas duct 27. A part of the exhaust gas flowing through the exhaust passage 3 is diffused by the diffusion resistance layer 24, and in this condition flows into the exhaust gas duct 27 so as to contact the exhaust side electrode 22. The diffusion resistance layer 24 is formed from a porous ceramic or the like, for example.

The atmosphere side electrode 23 is disposed within an atmosphere duct 25 that communicates with the atmosphere. Atmospheric air flowing into the atmosphere duct 25 contacts the atmosphere side electrode 23.

The exhaust side electrode 22 and the atmosphere side electrode 23 are platinum electrodes.

When a detection voltage V is applied between the exhaust side electrode 22 and the atmosphere side electrode 23 of the air-fuel ratio sensor 9, configured as described above, by a battery (voltage applying means) 28, a current corresponding to the oxygen concentration of the exhaust gas flows through the air-fuel ratio sensor 9.

For example, when the air-fuel ratio of the exhaust gas is rich, oxygen in the atmosphere duct 25 forms oxygen ions in response to an electrode reaction by the atmosphere side electrode 23, and these oxygen ions move through the solid electrolyte layer 21 from the atmosphere side electrode 23 to the exhaust side electrode 22, as indicated by arrows in FIG. 2. On the exhaust side electrode 22 side, the oxygen ions that have moved thereto react with HC, CO, and H2 in the exhaust gas duct 27 so as to generate carbon dioxide and water.

When the air-fuel ratio of the exhaust gas is lean, meanwhile, surplus oxygen in the exhaust gas forms oxygen ions in response to an electrode reaction by the exhaust side electrode 22, and these oxygen ions move through the solid electrolyte layer 21 from the exhaust side electrode 22 to the atmosphere side electrode 23. When the oxygen ions reach the atmosphere side electrode 23, electrons separate therefrom such that the oxygen ions return to oxygen, and this oxygen is discharged into the atmosphere duct 25.

As described above, a current flows between the exhaust side electrode 22 and the atmosphere side electrode 23 in accordance with the movement of the oxygen ions, and the value of the current that flows at this time varies in accordance with the air-fuel ratio of the exhaust gas.

Figure 3:
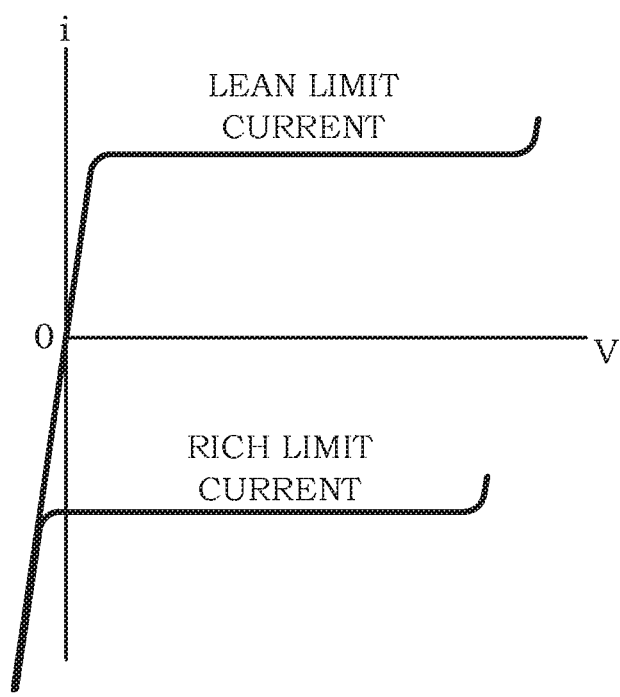
FIG. 3 is a diagram showing a voltage-current characteristic of the air-fuel ratio sensor.

FIG. 3 is a diagram showing a voltage-current characteristic of the air-fuel ratio sensor 9 described above. The abscissa shows the applied voltage, and the ordinate shows the output current.

As shown in FIG. 3, a region in which the value of the output current does not vary even in response to variation in the applied voltage exists both when the air-fuel ratio is lean and when the air-fuel ratio is rich. This applied voltage region in which the output current value does not vary will be referred to as a "limit current region", and the output current value in the limit current region will be referred to as a "limit current value".

The limit current value is commensurate with the air-fuel ratio of the exhaust gas, and therefore the air-fuel ratio can be detected on the basis of the magnitude of the limit current value.

On the basis of the air-fuel ratio detected in this manner, the ECU 13 executes feedback control on the fuel injection amount to align the air-fuel ratio of the exhaust gas with the target air-fuel ratio (the stoichiometric air-fuel ratio, for example).

Incidentally, the reason why the air-fuel ratio of the exhaust gas can be detected using the air-fuel ratio sensor 9 is because the oxygen ions move through the solid electrolyte layer 21, as described above. Therefore, when the air-fuel ratio of the exhaust gas is rich such that the amount of oxygen supplied to the atmosphere side electrode 23 becomes insufficient, the amount of oxygen ion movement becomes smaller than an amount of movement corresponding to the air-fuel ratio, and as a result, the detection value obtained by the air-fuel ratio sensor 9 becomes leaner than the actual air-fuel ratio. The air-fuel ratio sensor 9 is structurally limited in terms of the capacity of the atmosphere duct 25, an atmospheric air introduction path, and so on, and therefore a speed at which atmospheric air flows into the atmosphere duct 25 is limited. Accordingly, a deficiency in the amount of oxygen supplied to the atmosphere side electrode 23 is steadily more likely to occur as the air-fuel ratio of the exhaust gas increases in richness.

Figure 4:
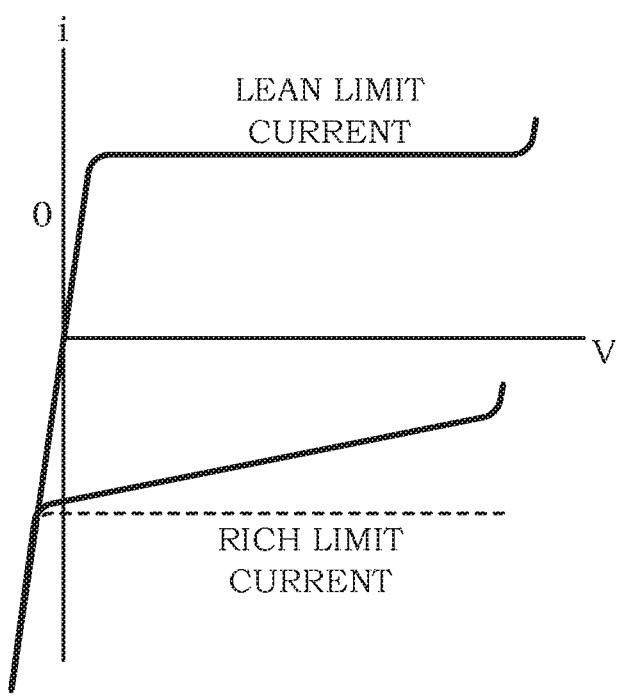
FIG. 4 is a diagram showing the voltage-current characteristic of the air-fuel ratio sensor when the control precision deteriorates due to an oxygen supply amount deficiency.

FIG. 4 is a diagram showing the voltage-current characteristic in a case where the amount of oxygen supplied to the atmosphere side electrode 23 is insufficient. As shown in the figure, on the rich side, the output current value increases in proportion to the applied voltage. When the limit current value stops being flat in this manner, the air-fuel ratio detection precision deteriorates.

Hence, to suppress a reduction in the precision of the air-fuel ratio control caused by a reduction in the detection precision of the air-fuel ratio sensor 9, the ECU 13 executes a control routine described below.

Figure 5:
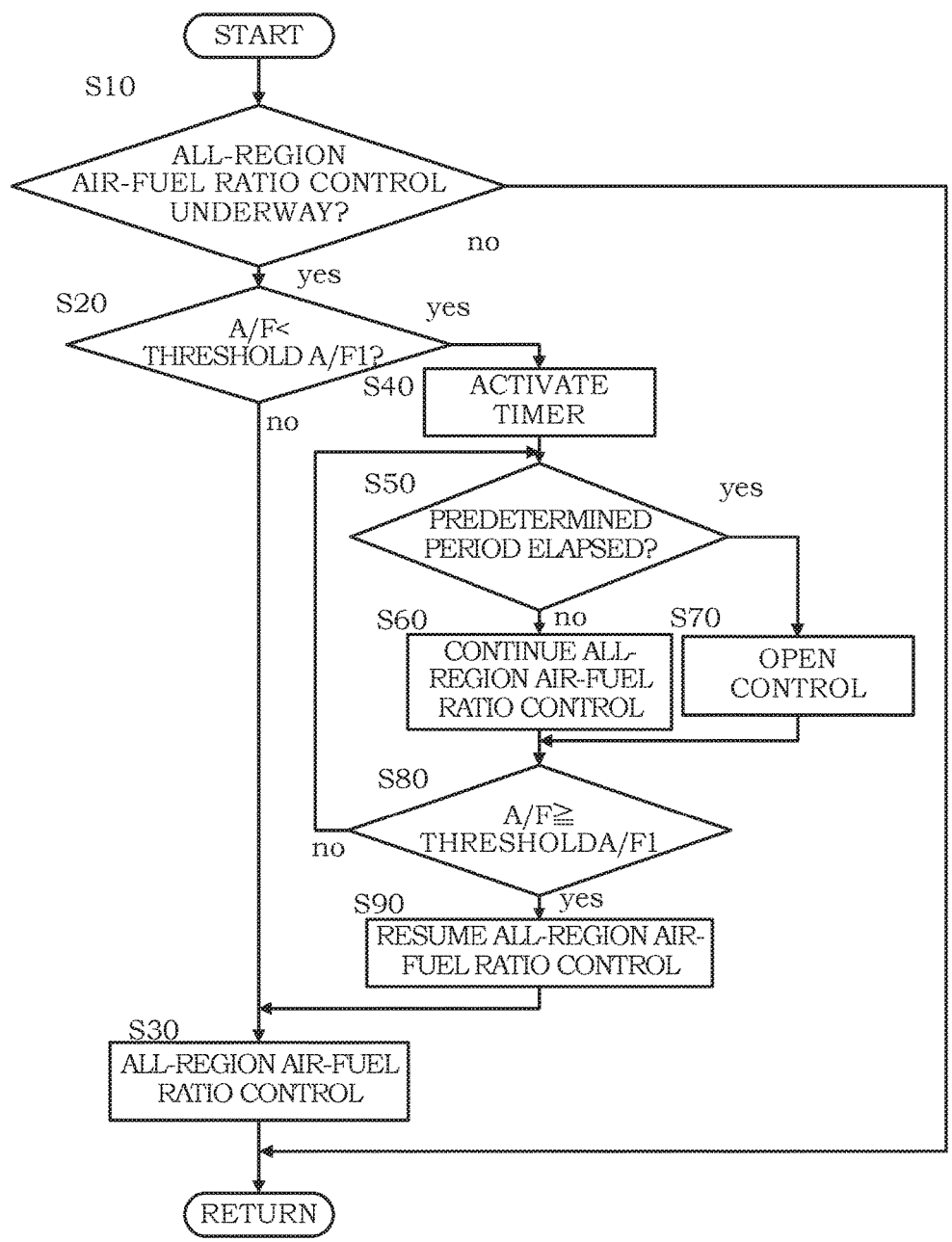
FIG. 5 is a flowchart showing a control routine of air-fuel ratio control.

FIG. 5 shows a control routine of air-fuel ratio control executed by the ECU 13.

In step S10, the ECU 13 determines whether or not all-region air-fuel ratio control is underway. When all-region air-fuel ratio control is not underway, the ECU 13 terminates the current routine as is, and when all-region air-fuel ratio control is underway, the ECU 13 executes processing of step S20. "All-region air-fuel ratio control" is air-fuel ratio feedback control based on the detection value of the air-fuel ratio sensor 9, and is executed by controlling the fuel injection amount so as to realize a target air-fuel ratio set in accordance with the engine operating state. It should be noted that here, the target air-fuel ratio is not limited to the stoichiometric air-fuel ratio. During acceleration, for example, a rich target air-fuel ratio may be set in order to generate higher torque.

To execute the all-region air-fuel ratio control, the air-fuel ratio sensor 9 must be in an active condition. In this step, therefore, when the air-fuel ratio sensor 9 is not in an active condition, for example during a warm-up operation following a cold start, all-region air-fuel ratio control is determined not to be underway.

In step S20, the ECU 13 determines whether or not the air-fuel ratio (A/F) of the exhaust gas is smaller than a threshold A/F1. When the air-fuel ratio equals or exceeds the threshold A/F1, the ECU 13 executes processing of step S30, and when the air-fuel ratio is smaller than the threshold A/F1, the ECU 13 executes processing of step S40. The threshold A/F1 used in this step is an air-fuel ratio at which the amount of oxygen supplied to the atmosphere side electrode of the air-fuel ratio sensor does not become insufficient when an operation is continued at that air-fuel ratio, or in other words an air-fuel ratio at which the detection precision of the air-fuel ratio sensor 9 does not deteriorate. The threshold A/F1 is set in accordance with the structure of the air-fuel ratio sensor 9, for example the capacity of the atmosphere duct 25, the atmospheric air introduction path, and so on. In this embodiment, a detectable A/F to be described below is set as the threshold A/F1.

In step S30, which is executed when the air-fuel ratio equals or exceeds the threshold A/F1, the ECU 13 continues the all-region air-fuel ratio control as is.

When the air-fuel ratio is smaller than the threshold A/F1, the ECU 13 activates a timer in step S40, and then determines in step S50 whether or not a predetermined period set in advance has elapsed.

Here, the predetermined period will be described.

Figure 6:
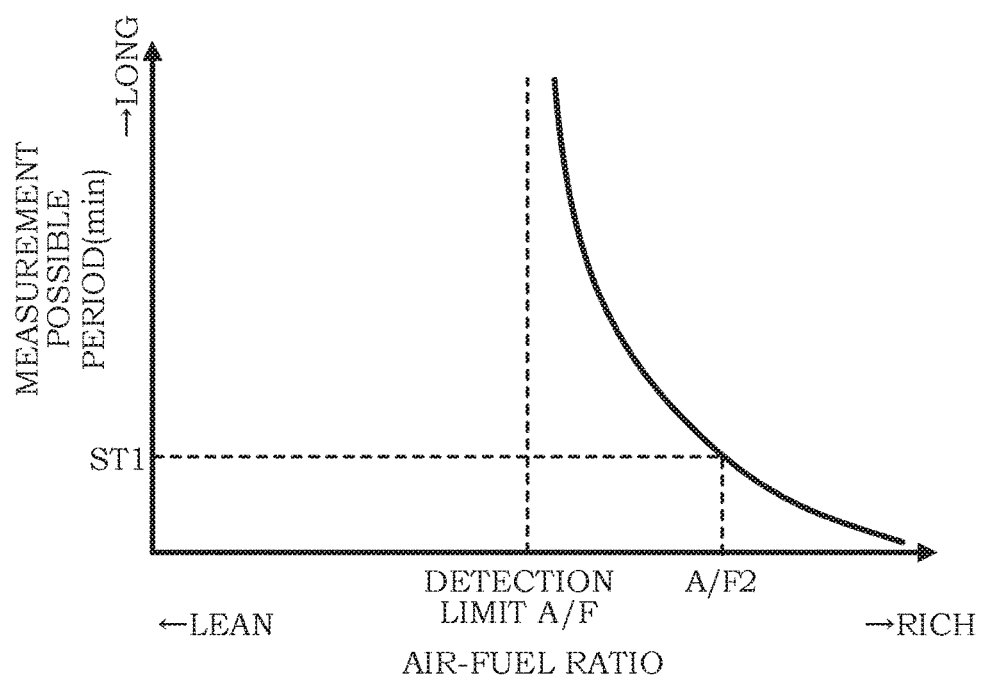
FIG. 6 is a diagram showing a relationship between an air-fuel ratio of exhaust gas and a measurement possible period of the air-fuel ratio sensor.

FIG. 6 is a diagram showing a relationship between the air-fuel ratio of the exhaust gas and a measurement possible period during which the air-fuel ratio can be measured by the air-fuel ratio sensor 9, this relationship having been discovered by the inventor of the present invention. The measurement possible period is a period during which the air-fuel ratio sensor 9 can detect the air-fuel ratio accurately.

As described above, when the air-fuel ratio of the exhaust gas is rich such that the amount of oxygen supplied to the atmosphere side electrode 23 becomes insufficient due to limitations in the capacity of the atmosphere duct 25 and so on, the air-fuel ratio sensor 9 is unable to detect the air-fuel ratio accurately.

When a rich side limit air-fuel ratio at which the amount of oxygen supplied to the atmosphere side electrode 23 does not become insufficient during air-fuel ratio detection is set as a detection limit A/F and the air-fuel ratio remains on the lean side of the detection limit A/F, the measurement possible period of the air-fuel ratio sensor 9 is theoretically infinite.

Even when the air-fuel ratio is on the rich side of the detection limit A/F, however, the detection precision of the air-fuel ratio sensor 9 does not deteriorate immediately. For example, when the air-fuel ratio varies from the lean side of the detection limit A/F to the rich side, the atmosphere duct 25 is still full of atmospheric air immediately after the variation, and therefore the amount of oxygen supplied to the atmosphere side electrode 23 does not immediately become insufficient. In other words, the air-fuel ratio sensor 9 can detect the air-fuel ratio precisely for as long as the oxygen supply to the atmosphere side electrode 23 is covered by the air in the atmosphere duct 25. To put it another way, when the air-fuel ratio of the exhaust gas is richer than the detection limit A/F, the measurement possible period of the air-fuel ratio sensor 9 steadily shortens as the richness increases.

The characteristics described above, i.e. that the detection precision of the air-fuel ratio sensor 9 does not deteriorate as soon as the air-fuel ratio shifts to the rich side of the detection limit A/F, and that the time (the measurement possible period) required for the detection precision to deteriorate is determined in accordance with the air-fuel ratio, were discovered by the inventor.

Hence, in this embodiment, on the basis of the characteristics described above, the predetermined period is set in accordance with the air-fuel ratio, and a measurement possible period ST1 at an air-fuel ratio A/F2 is set as the predetermined period. When the predetermined period ST1 is set in this manner, an air-fuel ratio on the lean side of the air-fuel ratio A/F2 can be detected precisely for the predetermined period ST1. The specific predetermined period ST1 is set in accordance with the structure of the air-fuel ratio sensor 9 and the vehicle type to which this embodiment is applied, but is generally approximately several tens of seconds to several minutes long.

Description of the flowchart will now be continued.

The ECU 13 executes processing of step S60 after determining in step S50 that the predetermined period ST1 has not yet elapsed, and executes processing of step S70 after determining that the predetermined period ST1 has elapsed.

In step S60, the ECU 13 continues the all-region air-fuel ratio control. The reason for this is that the measurement possible period of the air-fuel ratio sensor does not elapse until the predetermined period ST1 elapses.

In step S70, meanwhile, the ECU 13 prohibits the all-region air-fuel ratio control, and executes open loop control based on the target air-fuel ratio. The reason for this is that when the all-region air-fuel ratio control is executed in a condition where the detection precision of the air-fuel ratio sensor 9 has deteriorated, the precision with which the air-fuel ratio is controlled deteriorates.

In step S80, the ECU 13 determines whether or not the air-fuel ratio A/F has returned to or above the threshold A/F1. When the air-fuel ratio A/F has returned, the ECU 13 executes processing of step S90, and when the air-fuel ratio A/F has not returned, the ECU 13 executes the processing of step S50.

In step S90, the ECU 13 determines that the all-region air-fuel ratio control is to be resumed, and executes the processing of step S30. It should be noted that when the processing advances from step S60 to step S90 via step S80, the ECU 13 determines that the all-region air-fuel ratio control is to be continued.

As described above, in a situation where the precision with which the air-fuel ratio of the exhaust gas is detected may deteriorate due to the structural limitations of the air-fuel ratio sensor 9, the all-region air-fuel ratio control is continued for the predetermined period during which the air-fuel ratio sensor 9 can detect the air-fuel ratio precisely.

When the predetermined period elapses, the all-region air-fuel ratio control is prohibited, and the open loop control is executed instead. Further, when the air-fuel ratio reaches or exceeds the threshold A/F1 after switching to the open loop control, the all-region air-fuel ratio control is resumed.

Figure 7:
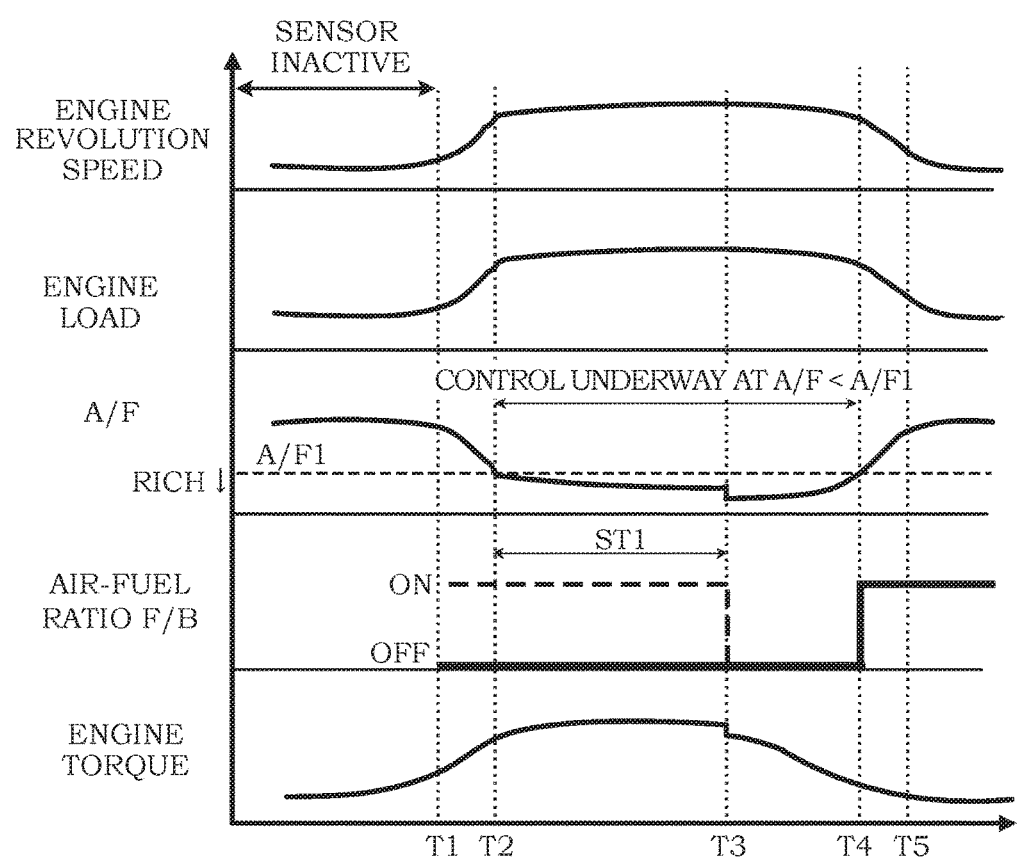
FIG. 7 is a timing chart showing a case in which the control routine of FIG. 5 is executed.

FIG. 7 is an example of a timing chart showing a case in which the control routine of FIG. 5 is executed. On the chart of the air-fuel ratio feedback control, dotted lines show a case in which the control according to this embodiment is executed, and solid lines show a case in which the control according to the prior art is executed.

Prior to a timing T1, the air-fuel ratio sensor 9 is not in an active condition, and therefore the all-region air-fuel ratio control (the air-fuel ratio feedback control) is not executed.

When the air-fuel ratio sensor 9 enters the active condition at the timing T1, the all-region air-fuel ratio control is started. Further, from the timing T1, the vehicle starts to accelerate, and therefore an engine load increases, leading to an increase in the richness of the air-fuel ratio. The reason why the air-fuel ratio increases in richness is that the target air-fuel ratio is switched to a so-called output air-fuel ratio or a value in the vicinity of the output air-fuel ratio in order to generate higher torque.

When the target air-fuel ratio becomes richer than the threshold A/F1 at a timing T2, the all-region air-fuel ratio control is continued in a condition where the timer is activated.

At a timing T3, at which the predetermined period ST1 elapses following activation of the timer, the all-region air-fuel ratio control is switched to the open loop control. At the time of the switch, the air-fuel ratio varies in step fashion, the reason being that after switching to the open loop control, it is no longer possible to absorb variation in the fuel injection amount caused by individual differences in components such as the fuel injection valve. Therefore, depending on the magnitude of this variation, the air-fuel ratio may not vary in step fashion at the timing T3.

When the air-fuel ratio of the exhaust gas exceeds A/F1 at a timing T4 after switching to the open loop control, the open loop control is switched to the all-region air-fuel ratio control.

According to this embodiment, as described above, the air-fuel ratio can be feedback-controlled for the predetermined period even at an air-fuel ratio at which the detection precision of the air-fuel ratio sensor 9 may deteriorate due to a deficiency in the amount of oxygen supplied to the atmosphere side electrode 23, for example the output air-fuel ratio or an air-fuel ratio in the vicinity thereof. As a result, improvement effects are obtained in terms of every one of output, fuel efficiency, and exhaust emissions in comparison with a case where the all-region air-fuel ratio control is switched to the open loop control as soon as the air-fuel ratio enters this region.

Next, actions and effects obtained with this embodiment will be summarized.

The air-fuel ratio control device according to this embodiment includes the air-fuel ratio sensor 9 configured such that the output current value thereof varies linearly in accordance with the oxygen concentration, and the ECU 13 (air-fuel ratio feedback means, prohibiting means) for implementing feedback control on the air-fuel ratio on the basis of the detection value of the air-fuel ratio sensor 9, and prohibiting the feedback control when the air-fuel ratio equals or exceeds a predetermined rich air-fuel ratio. The air-fuel ratio control device permits the feedback control for the predetermined period after the air-fuel ratio reaches or exceeds the predetermined rich air-fuel ratio. Here, the predetermined rich air-fuel ratio is an air-fuel ratio at which the amount of oxygen supplied to the atmosphere side electrode of the air-fuel ratio sensor becomes insufficient when an operation is continued at that air-fuel ratio.

Therefore, the air-fuel ratio feedback control can be executed even in a situation where the amount of oxygen supplied to the atmosphere side electrode 23 is insufficient due to the structural limitations of the air-fuel ratio sensor 9 such that the air-fuel ratio detection precision may deteriorate, for example when a rich target air-fuel ratio such as the output air-fuel ratio is required. As a result, improvements in the output, fuel efficiency, and exhaust emissions can be achieved in comparison with a case where the open loop control is executed in the same situation.

In this embodiment, the open loop control having the predetermined air-fuel ratio as the target value is executed after the air-fuel ratio feedback control is prohibited. In so doing, a deviation between the actual air-fuel ratio and the target air-fuel ratio can be suppressed even in a condition where the detection precision of the air-fuel ratio sensor 9 has deteriorated.

The predetermined period according to this embodiment is set to be shorter than the time required for the air-fuel ratio detection precision to deteriorate due to a deficiency in the amount of oxygen supplied to the atmosphere side electrode of the air-fuel ratio sensor. Therefore, a situation in which the air-fuel ratio feedback control is executed on the basis of an air-fuel ratio detected with a low degree of detection precision can be prevented.

In this embodiment, the internal combustion engine 1 includes the turbocharger 10, and the air-fuel ratio sensor 9 is provided in the exhaust passage 3 on the upstream side of the turbine 10B. Thus, the air-fuel ratio sensor 9 detects the air-fuel ratio of the exhaust gas before mixing has progressed, making cylinder differentiation easier. As a result, the air-fuel ratio control can be executed in accordance with variation among the cylinders in the fuel injection amount and so on.

In this embodiment, the air-fuel ratio sensor 9 is configured to include the solid electrolyte layer 21 through which oxygen ions can move, the exhaust side electrode 22 provided on the exhaust side of the solid electrolyte layer 21 so as to be exposed to the exhaust passage 3 of the internal combustion engine 1, the atmosphere side electrode 23 provided on the atmosphere side of the solid electrolyte layer 21 so as to be exposed to the atmosphere, and the voltage applying means 28 for applying a voltage between the exhaust side electrode 22 and the atmosphere side electrode 23. Hence, the air-fuel ratio sensor 9 is configured such that the output current value thereof varies linearly in accordance with the oxygen concentration of the exhaust gas, and is therefore capable of detecting the air-fuel ratio over a wide range.

The length of the predetermined period according to this embodiment is set in accordance with the air-fuel ratio. In so doing, the predetermined period can be set appropriately in accordance with the measurement possible period, which is different at each air-fuel ratio. As a result, the air-fuel ratio feedback control can be implemented continuously for a longer time.

It should be noted that in the above description, the so-called atmospheric air introduction type air-fuel ratio sensor 9 is used, but this embodiment may also be applied to a case in which a type that generates oxygen by means of an oxygen pump layer provided in the element 20 is used. The reason for this is that a situation in which oxygen generation cannot keep up with an enriched air-fuel ratio such that the amount of oxygen supplied to the atmosphere side electrode 23 becomes insufficient may occur similarly when the air-fuel ratio sensor 9 is of a type having an oxygen pump layer.

An embodiment of the present invention was described above, but the above embodiment merely illustrates some examples of applications of the present invention, and the technical scope of the present invention is not limited to the specific configurations of the above embodiment.

The invention claimed is:

1. An air-fuel ratio control device comprising:
   an air-fuel ratio sensor configured such that an output current value thereof varies linearly in accordance with an oxygen concentration;
   an air-fuel ratio feedback control unit for feedback-controlling an air-fuel ratio on the basis of a detection value from the air-fuel ratio sensor; and
   a prohibiting unit for prohibiting the feedback control when the air-fuel ratio is smaller than a predetermined rich air-fuel ratio,
   wherein the feedback control is permitted for a predetermined period after the air-fuel ratio becomes smaller than the predetermined rich air-fuel ratio.

2. The air-fuel ratio control device as defined in claim 1, wherein the predetermined rich air-fuel ratio is an air-fuel ratio at which an amount of oxygen supplied to an atmosphere side electrode of the air-fuel ratio sensor becomes insufficient when an operation is continued at the air-fuel ratio.

3. The air-fuel ratio control device as defined in claim 1, wherein open loop control having a predetermined air-fuel ratio as a target value is executed after the air-fuel ratio feedback control is prohibited.

4. The air-fuel ratio control device as defined in claim 2, wherein the predetermined period is set to be shorter than a time required for an air-fuel ratio detection precision to deteriorate due to a deficiency in the amount of oxygen supplied to the atmosphere side electrode of the air-fuel ratio sensor.

5. The air-fuel ratio control device as defined in claim 1, wherein an internal combustion engine includes a turbocharger, and
   the air-fuel ratio sensor is provided in an exhaust passage on an upstream side of a turbine of the turbocharger.

6. The air-fuel ratio control device as defined in claim 1, wherein the air-fuel ratio sensor is configured to include:
   a solid electrolyte layer through which oxygen ions can move;
   an exhaust side electrode provided on an exhaust side of the solid electrolyte layer so as to be exposed to an exhaust passage of an internal combustion engine;
   the atmosphere side electrode, which is provided on an atmosphere side of the solid electrolyte layer so as to be exposed to the atmosphere; and
   a voltage applying unit for applying a voltage between the exhaust side electrode and the atmosphere side electrode.

7. The air-fuel ratio control device as defined in claim 1, wherein a length of the predetermined period is set in accordance with the air-fuel ratio.

8. An air-fuel ratio control device comprising:
   an air-fuel ratio sensor configured such that an output current value thereof varies linearly in accordance with an oxygen concentration;
   air-fuel ratio feedback control means configured to implement feedback control on an air-fuel ratio on the basis of a detection value from the air-fuel ratio sensor; and
   prohibiting means configured to prohibit the feedback control when the air-fuel ratio is smaller than a predetermined rich air-fuel ratio,
   wherein the feedback control is permitted for a predetermined period after the air-fuel ratio becomes smaller than the predetermined rich air-fuel ratio.

9. An air-fuel ratio control method comprising:
   executing air-fuel ratio feedback control for feedback-controlling a fuel injection amount on the basis of a detection value from an air-fuel ratio sensor in order to set exhaust gas of an internal combustion engine at a predetermined air-fuel ratio, the air-fuel ratio sensor being configured such that an output current value thereof varies linearly in accordance with an oxygen concentration; and
   when the air-fuel ratio becomes smaller than a predetermined rich air-fuel ratio, permitting the feedback control for a predetermined period after the air-fuel ratio becomes smaller than the predetermined rich air-fuel ratio, and prohibiting the feedback control once the predetermined period has elapsed.

* * * * *